United States Patent [19]

Inokuma et al.

[11] Patent Number: 5,018,915
[45] Date of Patent: May 28, 1991

[54] SPINDLES OF MACHINE TOOLS

[75] Inventors: Takahiko Inokuma, Yokohama; Sadamu Baba, Numazu; Shoji Imao, Tajimi; Hitoshi Kodama, Nagoya; Takeo Gomi, Toyohashi, all of Japan

[73] Assignees: Toshiba Kikai Kabushiki Kaisha; Mitsubishi Rayon Company, Ltd., both of Tokyo, Japan

[21] Appl. No.: 497,621

[22] Filed: Mar. 23, 1990

[30] Foreign Application Priority Data

Sep. 8, 1989 [JP] Japan .................. 1-234218

[51] Int. Cl.[5] .............. B23C 9/00; B23B 47/00
[52] U.S. Cl. .................... 409/231; 408/238
[58] Field of Search ............ 409/231, 232, 233, 234; 74/214; 408/238; 51/134.5 R, 166 MH

[56] References Cited

U.S. PATENT DOCUMENTS

| | | | |
|---|---|---|---|
| 3,678,632 | 7/1972 | Eversole et al. | 409/231 |
| 3,907,729 | 9/1975 | Burkey et al. | 74/214 X |
| 4,072,084 | 2/1978 | Knight, Jr. et al. | 409/234 |

FOREIGN PATENT DOCUMENTS

| | | | |
|---|---|---|---|
| 175064 | 3/1986 | European Pat. Off. | 409/231 |
| 165101 | 1/1985 | Japan | 409/231 |
| 1136747 | 6/1986 | Japan | 409/231 |

Primary Examiner—William Briggs
Attorney, Agent, or Firm—Oblon, Spivak, McClelland, Maier & Neustadt

[57] ABSTRACT

In a spindle of a machine tool, a cylindrical member of the spindle adapted to accommodate the shank of a tool is prepared by winding carbon or glass fiber and the wound fiber is impregnated with a heat curable resin. After curing the resin a protective coating layer is applied to the other surface of the cylindrical member.

11 Claims, 1 Drawing Sheet

SPINDLES OF MACHINE TOOLS

BACKGROUND OF THE INVENTION

This invention relates to a spindle of a machine tool, and more particularly a spindle capable of not using as far as possible metal materials but decreasing the weight of the spindle and the adverse effect of linear thermal expansion.

As the material of the spindle utilized for a machining center, a boring machine, and a milling machine has generally been used steel or alloy steels having a large weight because steel and alloy steels have a high Young's modulus, can harden their surfaces, easy to machine and are not expensive.

The linear expansion coefficient of steel lies in a range of $11 \sim 16 \times 10^{-6°}$ $C^{-1}$. Thus, in a spindle having a length of 2 m, when the temperature varies by 10° C., the length of the spindle would vary in a range of $2.2 \sim 3.2 \times 10^{-1}$ mm. For example, during the operation of a boring machine, where the temperature of the spindle rises by 10° C. from the start to the end of the machining, the cut depth would vary by about 0.3 mm, thus failing to obtain machined products having high dimensional accuracies. Moreover, since steel has a large specific gravity and the weight of the spindle made of steel increases, thus resulting in a large deformation due to centrifugal force at the time of high speed operation as well as in the nonuniformity of the dimensions of the machined products. Furthermore, as the vibration attenuation of steel is small, a spindle made of steel is not suitable for high speed rotation. Furthermore, where the spindle weight is large it takes longer time for building up to a high speed which requires provision of a large power source.

As materials having a small weight and a high rigidity have been known such fiber reinforced composite materials as carbon fiber reinforced plastic material (CFRP), and such materials are now being used in many industrial fields. However, the fields capable of using such materials have been limited. Usually, these materials have been used for producing products for use in public welfare and members for use in aeroplanes and it has been extremely rare to use these materials as structural members of machines. As special examples, rollers are made of these materials as disclosed in Japanese Laid Open Patent Specification No. 194197/1986 and Japanese Laid Open Utility Model Specification No. 69812/1988. These rollers were developed to have specific characteristics not found in the prior art metal rollers. More particularly, the composite materials described above, particularly CFRP was used to manufacture rollers by noting its specific characteristics, that is an extremely light weight and a high rigidity. However, these rollers are constructed to be supported at both ends so that they are used in paper making machines, printing machines, synthetic resin film manufacturing machines, etc. These rollers have been used in these machines because it is possible to minimize as far as possible the flexure at the central portion of the roller, and can accurately follow the speed variation at the time of quickly stopping the roller and varying the speed of the roller. These fiber reinforced composite materials do not have sufficient mechanical strength capable of withstanding mechanically severe conditions. For this reason, although rollers disclosed in Japanese Laid Open specifications described above are applicable to certain industrial fields, they cannot be used as structural members subjected to severe operating conditions, especially as a spindle of a machine tool.

When cutting or grinding metal material or hard and brittle material such as ceramics, the spindle of a machine tool is subjected to a heavy load in all directions. Moreover as the spindle has a cantilever construction, steel or alloy steels have been exclusively used for the spindle for the reason that these materials have high degrees of elasticity and rigidity, and can readily harden their surfaces. It has been recognized that it is impossible to practically use fiber reinforced plastic material having low hardness and low wear resistant property, although it is light and has a high rigidity.

As disclosed in Japanese Laid Open Patent Specification No. 96311/1988, use of carbon/carbon (C/C) composite material similar to the fiber reinforced plastic material for the manufacture of the spindle of a machine tool has been proposed.

The C/C composite material has been used for many years for preparing machine parts, parts of a nuclear reactor and space machines (see "Carbon Fiber" published on Nov. 1, 1955, authors: Otani and Kimura, by Kindai Henshusha, Japan). Although the inventors of this invention have also tried to apply the C/C composite material to the spindle of a machine tool it was found that this material is not suitable for such use. Consequently, the inventors have determined to use the fiber reinforced plastic material.

The C/C composite material can be obtained by pyrolyzing the fiber reinforced plastic composite material at a high temperature for carbonizing plastic material used as a matrix. However, the resulting C/C composite material has inferior physical characteristics, so that it is necessary to subject the C/C composite material to an additional processing for improving its physical characteristics. But to obtain desired characteristics it is necessary to use many steps of working, resulting in cost up.

The spindle made of steel has a poor dimensional stability due to a high linear expansion coefficient inherent to steel. Although it is possible to reduce the linear expansion coefficient by using metals other than steel for example, an invar alloy having a smallest linear expansion coefficient of $1 \sim 3 \times 10^{-6°}$ $C^{-1}$, invar is difficult to machine. The invar alloy cannot be used as the main material of a spindle because of its high cost and low hardness.

Since a spindle made of steel has a large weight, the spindle deforms greatly due to the centrifugal force created at the time of high speed running and since the attenuation characteristic of spindle vibration is poor, the quality of machined products and the machining accuracy are poor. Moreover, since the spindle made of steel has a large moment of inertia, it is difficult to increase the machining speed. Moreover the heavy steel spindle requires a large driving power and generates a large quantity of heat which decreases the machining accuracy.

In order to obtain a spindle using the C/C composite material it is necessary to use a number of process steps which increases the manufacturing cost.

In Japanese Laid Open Utility Model Specification No. 165101/1985 is disclosed a spindle of a machine tool utilizing a hollow cylinder shaped fiber reinforced plastic material. In this reference, the hollow cylinder is interposed between a tapered shank driven by a driving source and a tool holder made of steel and adapted to hold a tool. With this construction, the hollow cylinder is not used to directly receive the shank of the tool so that the advantage of the fiber reinforced composite material is not fully utilized.

SUMMARY OF THE INVENTION

It is an object of this invention to provide a novel spindle of a machine tool capable of reducing the weight of the spindle and reducing the linear elongation due to heat.

Another object of this invention is to provide a novel spindle of a machine tool capable of reducing the linear expansion coefficient and the weight of the spindle.

Still another object of this invention is to provide a novel spindle of a machine tool capable of readily manufactured at a low cost.

According to this invention there is provided a spindle of a machine tool characterized by comprising an adapter made of metal and provided with a conical opening at one end and adapted to receive a conical portion of a shank of a tool, a hollow cylindrical member made of fiber reinforced composite material connected to the other end of the adapter to extend coaxially therewith for accommodating the shank, and a protective coating layer applied onto the outer surface of the spindle.

DESCRIPTION OF THE PREFERRED EMBODIMENTS

Figure 1:
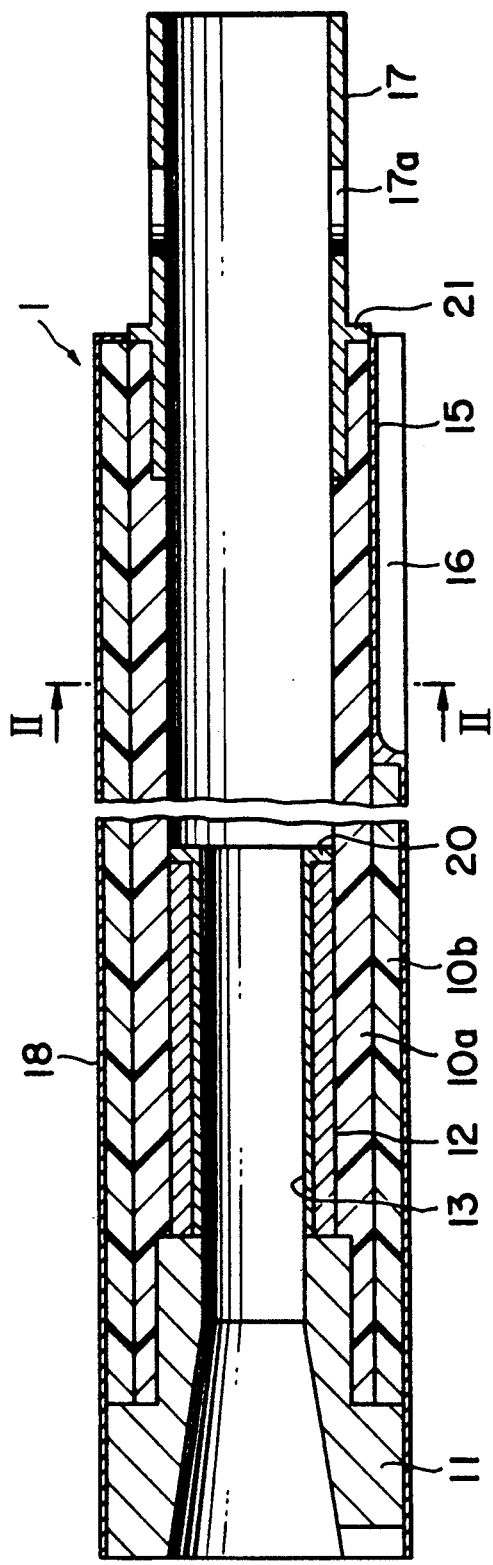
FIG. 1 is a longitudinal sectional view of a spindle of a machine tool the invention.

Before describing the construction of the spindle of this invention with reference to the accompanying drawings, essential features, functions and advantages of this invention will firstly be described.

As above described, CFRP has advantageous characteristic for use in the spindle of a machine tool.

Taking the spindle of a boring machine as an example, chips are liable to adhere to the surface of the spindle so that the surface will be damaged unless the surface is sufficiently hard. The hardness of CFRP is governed by that of the matrix resin. However, since the hardness of the matrix resin is generally low the surface of the spindle would be damaged.

To use CFRP for the spindle of a machine tool the CFRP should satisfy all requirements of the spindle while obviating disadvantages of a spindle made of steel.

Considering the thermal expansion of a hollow cylindrical member made of CFRP by suitably selecting the winding angle of a tape or filament of CFRP it was found that it is possible to make the linear expansion coefficient in the longitudinal direction of the hollow cylindrical member to be minus or zero, or limit the absolute value of the linear expansion coefficient to 0.5 $\times 10^{-6°}$ $C^{-1}$. Carbon fibers are suitable for preparing fiber reinforced composite material, but Aramide fibers can be used.

With a hollow cylindrical member made of CFRP, linear expansion coefficient as shown in Table I can generally be obtained in accordance with the winding angle of the fibers, although more or less different depending upon the type of fiber and resin used.

As shown in Table I the CFRP has a negative linear expansion coefficient when the winding angle of the fiber is small, but as the winding angle of the fiber increases the linear expansion coefficient becomes positive. Consequently, where a suitable combination of different winding angles is used, or a specific winding angle is used, it is theoretically possible to make zero or negative the linear expansion coefficient of the hollow cylindrical member.

TABLE I

| Winding angle (degree) | Linear expansion coefficient ($°C.^{-1}$) |
|---|---|
| 0 | $-0.7 \times 10^{-6}$ |
| ±45 | $2.0 \times 10^{-6}$ |
| 90 | $24 \times 10^{-6}$ |

In a hollow cylindrical member which is an indispensable element of the spindle of this invention the absolute value of the linear expansion coefficient is made to be less than $0.5 \times 10^{-6°}$ $C^{-1}$ by suitably selecting the winding angle of carbon fiber. This hollow cylindrical member undergoes a dimensional variation of only $1 \times 10^{-2}$ mm even when the temperature of a spindle having a length of 2 m, for example, changes by 10° C. When the hollow cylindrical member made of CFRP is combined with steel or other metal member, it is possible to limit the linear expansion coefficient of the assembly to be less than $5 \times 10^{6°}$ $C^{-1}$ which means that cutting operation of extremely higher accuracy can be obtained than the conventional spindle made of steel having a linear expansion coefficient of $11 \sim 16 \times 10^{-6°}$ $C^{-1}$.

Important part of the spindle of this invention is made of the fiber reinforced composite material and a portion of the spindle is made of metal and ceramic. Certain portion of the carbon fibers may be substituted by glass fibers or Aramide fibers.

In most cases, in addition to the dimensional stability, the spindle is required to have an adequate bending rigidity and twisting rigidity. If only one fiber winding angle is selected for the purpose of making zero the linear expansion coefficient of the hollow cylindrical member it would become impossible to satisfy other necessary performances. However, by combining at least two winding angles of the fiber reinforced composite material, a number of methods can be used for making zero the linear expansion coefficient which increases the freedom of the design necessary to satisfy other performances. Where the fibers are wound at an angle of 0°, the highest value of the bending rigidity can be obtained. However, as it is difficult to wind the fiber at the angle of 0°, it is advantageous to wind the fiber at angles in a range of ±(10°~15°). Since machining is done by rotating the spindle or a workpiece, an optimum twisting rigidity is necessary. Where the spindle is made of CFRP, the maximum twisting rigidity can be obtained when the winding angle is ±45°. As a consequence, it is advantageous to include a layer wound at angles of ±45° in a laminated structure. When the departure of the actual winding angle from ±45° is taken into consideration, it is advantageous to wind the fiber at an angle in a range of ±(40°~50°).

In the spindle of this invention it is advantageous to use at least two angles of winding the fibers, one ±(0°~15°), and the other ±(40°~50°). The fiber reinforced composite member may be constituted by a single layer or a plurality of superposed layers. Other range of winding angles can also be used.

As above described, the spindle of a machine tool should have various characteristics, for example, a low thermal expansion coefficient, a large impact proofness, a high surface hardness, and no decrease in the mechanical strength when the spindle is machined.

The type of the carbon fiber may be either one of high strength type, medium elastic type and high elastic type, but where highly elastic carbon fibers are used, a spindle having a high degree of rigidity can be obtained. Among Aramide fibers are included fibers having negative linear expansion coefficient which are most suitable for the spindle of this invention. In addition to thermosetting resins, epoxy resin, phenol resin and polyester resin, vinyl ester resin and polyimide resin, for example, can be used. Among the thermoplastic resins are included nylon 66, polycarbonates, polyethyleneterephthalates, polyether ether ketones, polyether ketones, polyphenylene sulfides and polyether imides.

The method of winding the fiber reinforced composite material includes direct filament winding, sheet winding and roving winding.

A preferred example of this invention will now be described with reference to FIGS. 1 and 2, in which the inner and outer layers of a hollow cylindrical member prepared by winding CFRP at different angles are designated by 10a and 10b, respectively. The hollow cylindrical member constitutes an essential element of the spindle 1 of this invention. Outer end member or a tool adapter 11 of the spindle 1 has a tapered or conical surface adapted to receive the conical portion of the shank of a tool. The adapter 11 is generally made of steel and a small diameter portion at its inner end is fitted in a recess formed at the inner surface of the inner layer 10a. An intermediate cylindrical member 12 made of invar having a very small linear expansion coefficient is bonded to the inner surface of the inner layer 10a. A hollow sleeve 13 made of steel and having a flange 20 at its inner end is snugly fitted in the inner surface of intermediate member 12.

As is well known, the spindle head of a conventional horizontal boring machine is constituted by a hollow cylindrical member, a conical surface formed at one end of the hollow cylindrical member for receiving a conical portion of the shank of a tool, a collet installed in the hollow cylindrical member for grasping a flange of the tool, a drawbar contained in the hollow cylindrical member for actuating the collet and a plurality of dish shaped springs encircling the drawbar for causing it to securely hold the tool. The spindle of this invention shown in FIGS. 1 and 2 can advantageously be applied to the spindle of the horizontal boring machine just described. In such application, the sleeve 13 has a length enough to accommodate the collet and the flange 20 engages the end surface the dish shaped springs.

The inner (right) end of the outer layer 10b is provided with a U shaped member 15 made of steel. The U shaped member 15 defines a key slot 16. A sleeve 17 made of steel is inserted into the inner end of the inner layer 10a. The sleeve 17 is provided with a flange 21 abutting the inner end surface of the inner layer 10a and a key groove 17a. The sleeve 17 has the same inner diameter as that of the inner layer 10a.

A coating or protective layer 18 made of hard metal or ceramic is applied onto the outer surface of the spindle 1.

EMBODIMENT 1

The hollow cylindrical member constituting the characterizing part of the spindle having an outer diameter of 110 mm, a length of 1590 mm and an inner diameter of 64.7 mm was prepared according to the filament winding method by using a medium elasticity type carbon fiber (Pylofil ® MM-1 made by Mitsubishi Rayon Co.) as the reinforcing fiber and an epoxy resin as the matrix. The inner layer 10a was wrapped at an angle of ±45°, whereas the outer layer 10b at an angle of ±10°. The thicknesses of these layers were 18.65 mm and 4 mm respectively. After completely curing the resin, component elements of the spindle were machined and ground and then assembled to obtain the spindle shown in FIG. 1. After assembling, the coating layer 18 was formed by successively electroplating copper and chromium and then the coating layer was ground. Alternatively, the protective coating 18 can be formed by flame coating such ceramics as $Al_2O_3$-$40TiO_2$ and chromina ($Cr_2O_3$). Since such flame coated protective film usually contains voids of 5~8% by volume, it is advantageous to fill such voids with plastic material or the like.

JIS (Japanese Industrial Standard) SACM645 was used to prepare the adaptor 11, invar was used for intermediate member 12, and JIS SCM (thermally refined steel) was used for the hollow sleeve 13, U shaped member 15 and the sleeve 17.

The purpose of using the intermediate member 12 made of invar is to prevent relative movement of the sleeve 13 and the inner layer 10a due to the difference in their linear expansion coefficients and to prevent peel off of the sleeve 13 and the inner layer 10a.

The spindle of this embodiment had a total length of 1815 mm, a weight of 32 kg, a bending rigidity (EI) of $6.4 \times 10^{10}$ kgf·mm$^2$, and a twisting rigidity (GIp) of $2.93 \times 10^{10}$ kgf·mm$^2$. The thermal expansion was found such that when the temperature was increased by 15° C., the dimensional variation was only $-9$ $\mu$ (contruction).

Table II shows a comparison of these characteristics of the spindle of this embodiment and a prior art spindle made of steel.

TABLE II

|  | This embodiment | Prior art |
| --- | --- | --- |
| Weight (Kg) | 32 | 92 |
| Bending rigidity kgf · mm$^2$ | $6.4 \times 10^{10}$ | $14.2 \times 10^{10}$ |
| Twisting rigidity kgf · mm$^2$ | $2.93 \times 10^{10}$ | $10.1 \times 10^{10}$ |
| Thermal expansion ($\mu$) at temperature rise of 15° C. | $-9$ | $+250$ |

1. When the weight of the spindle decreases to 32 kg from 92 kg there are the following merits.

(a) Due to inertial moment, the spindle control performance can be improved and the spindle can readily be operated at a higher speed.

The inertial moment of the spindle of this embodiment decreases to 25% of that of the prior art spindle made of steel so that the torque for increasing the speed of the spindle from standstill to a high speed in a given time decreases to only 25% of that of the prior art spindle made of steel.

This reduces the build up time to the high speed running whereby at the time of tapping, it becomes possible to repeatedly reverse the direction of rotation of the tap at a high speed. The torque necessary for accelerating the speed of a spindle to 3000 r.p.m. in a given time can be reduced to only 25% of that of the prior art spindle made of steel. This reduces the machining energy and the heat generation. As a consequence the energy and the heat displacement can be reduced.

(b) It is possible to improve the accuracy of spindle positioning.

In a machine tool having a spindle pay out mechanism, as the weight of the spindle has been reduced it is possible to reduce the slide resistance at the time of paying out the spindle. Moreover, since the twist angle of the driving system of the pay out mechanism is reduced, the positioning accuracy can be improved.

2. As can be noted from Table II, the rigidity of the spindle of this embodiment is lower than that of the prior art spindle. The bending rigidity and the twisting rigidity shown in Table II are sufficient for practical use.

Because the values of the prior art spindle were obtained for a product of Toshiba Kikai Kabushiki Kaisha and manufactured for cutting a workpiece at a low speed with a high torque. Spindles of the same class and utilized in a machining center require substantially the same torque as that of this embodiment (that is 75 kg·m). In other words, the spindle of this embodiment has sufficient rigidities.

3. Where the temperature rises by 15° C. the spindle of this embodiment contracts by 9 $\mu$, whereas the prior art spindle expands by 250 $\mu$.

This thermal expansion has a great influence upon the machining accuracy of openings. During use, the spindle is heated. For example, suppose now that openings are formed with a prior art spindle, the depth of the opening would become different due to the temperature rise of the spindle. More particularly the depth of the first opening (at this time there is only a little temperature rise of the spindle) and the depth of the ninth opening are different by 250 $\mu$ due to the temperature rise of 15° C. of the spindle. On the other hand, with the spindle of this embodiment the error in the depth of the opening is at most 10 $\mu$, thus enabling the machining at high accuracies. The elongation of the tool caused by heat generated during the use thereof, and the elongation of 15 $\mu$ of a tool having a length of 300 mm and used at a temperature rise of 5° C. are added together, the total elongation of the spindle and tool is expressed by 15 $\mu-9$ $\mu=6$ $\mu$ resulting in a better effect.

EMBODIMENT 2

Figure 2:
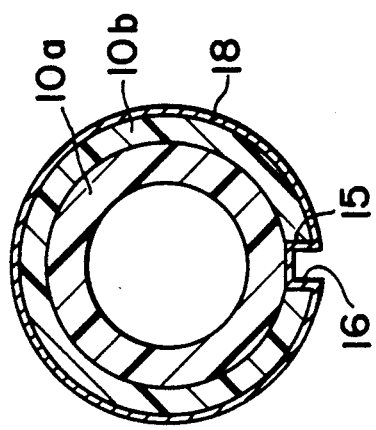
FIG. 2 is a view taken along a line II—II shown in FIG. 1.

The hollow cylindrical layers 10a and 10b of the spindle shown in FIG. 1 were constructed by winding fibers so as to have the same dimensions as those of embodiment 1. After sufficiently heat curing the resin the layers were finished and other elements made of steel and invar were secured to the hollow cylindrical members to complete a spindle. During assembling after machining, necessary parts are masked, and $Al_2O_3$-$40TiO_2$ is plasma coated to form a prime coating. Preferably the prime coating is formed by bond coating, an inorganic filler and epoxy resin. Then low viscosity epoxy resin is impregnated into the ceramic coating in vacuum and the resin is caused to set for 2 hours at a temperature of about 120° C. for sealing the interstice of the fibers with the resin.

The thermal expansion and rigidity of the spindle of this embodiment are substantially the same as those of embodiment 1.

EMBODIMENT 3

Fibers were wound by using the same material as embodiment 1 so as to make the fiber reinforced composite member to have the same dimension and shape as those of embodiment 1. After sufficiently setting the resin, the fiber reinforced composite member was machined, parts made of steel and an alloy same as those used in embodiment 1 were bonded to the fiber reinforced member and the assembly was machined. After applying a mask to necessary parts a prime coating was applied by flame coating technique. Then copper was flame coated onto the prime coating followed by sequential electroplating of copper and hard chromium. Then the resulting assembly was ground to have prescribed dimensions.

The thermal expansion and rigidity of the spindle of this embodiment were substantially equal to those of embodiment 1.

As has been described in detail since it is possible to decrease the weight of the spindle of a machine tool and the thermal expansion in the axial direction, the machining accuracy of the spindle can be improved. Decrease of the weight and the thermal expansion saves the operating power and increases the machining speed of the spindle.

What is claimed is:

1. A spindle of a machine tool comprising:
    an adapter made of metal and provided with a portion of a shank of a tool;
    a hollow cylindrical member made of fiber reinforced composite material and connected to the other end of said adapter to extend coaxially therewith for accommodating said shank, and
    a hard protective coating layer covering substantially the outer surface of said spindle including said member and said adapter.

2. The spindle according to claim 1 wherein said fiber is carbon fiber or Aramide fiber.

3. The spindle according to claim 1 wherein said hollow cylindrical member has an absolute linear expansion coefficient of less than $0.5 \times 10^{-6}$° $C^{-1}$ in a longitudinal direction of said hollow cylindrical member.

4. The spindle according to claim 1 wherein said fiber is wound at two or more angles.

5. The spindle according to claim 4 wherein one of the winding angles lies in a range of $0° \sim \pm 15°$ and the other lies in a range of $\pm(40° \sim 50°)$.

6. The spindle according to claim 1 further comprising a sleeve secured to an inner surface of said hollow cylindrical member.

7. The spindle according to claim 6 wherein said sleeve is made of metal.

8. The spindle according to claim 6 further comprising a cylindrical member made of invar and interposed between said sleeve and said hollow cylindrical member made of fiber reinforced composite material.

9. The spindle according to claim 6 wherein said sleeve is secured to said hollow cylindrical member by means of metal plating.

10. The spindle according to claim 6 wherein said sleeve is secured to said hollow cylindrical member by means of flame ceramic coating technique.

11. The spindle according to claim 10 wherein voids of a ceramic coating is sealed with a resin.

* * * * *